US012721612B2

(12) United States Patent
Duggal et al.

(10) Patent No.: US 12,721,612 B2
(45) **Date of Patent: *Sep. 1, 2026**

(54) MALLEABLE RETRACTOR

(71) Applicant: Illumix Surgical Canada Inc., Bright's Grove (CA)

(72) Inventors: Anil Duggal, Lexington, KY (US); Paul Dobrovolskis, Ancaster (CA); Roel H Kusters, Sittard (NL); Edsger Constant Pieter Smits, Eindhoven (NL)

(73) Assignee: Illumix Surgical, Bright's Grove (CA)

( * ) Notice: Subject to any disclaimer, the term of this patent is extended or adjusted under 35 U.S.C. 154(b) by 359 days.

This patent is subject to a terminal disclaimer.

(21) Appl. No.: 17/892,593

(22) Filed: Aug. 22, 2022

(65) Prior Publication Data

US 2023/0083792 A1 Mar. 16, 2023

Related U.S. Application Data

(63) Continuation of application No. 16/540,833, filed on Aug. 14, 2019, now Pat. No. 11,452,513, which is a (Continued)

(51) Int. Cl.
*A61B 17/02* (2006.01)
*A61B 90/30* (2016.01)
*A61B 17/00* (2006.01)

(52) U.S. Cl.
CPC .............. *A61B 17/02* (2013.01); *A61B 90/30* (2016.02); *A61B 2017/00017* (2013.01); *A61B 2017/00946* (2013.01); *A61B 2017/0225* (2013.01)

(58) Field of Classification Search
CPC . A61B 17/02; A61B 2017/0225; A61B 90/30; A61B 2090/304
(Continued)

(56) References Cited

U.S. PATENT DOCUMENTS 4,048,987 A 9/1977 Hurson
7,306,559 B2 12/2007 Williams
(Continued)

OTHER PUBLICATIONS

Edwards PD, Bull RK, Coulden R. CT measurement of main pulmonary artery diameter. Br J Radiol. Oct. 1998;71 (850):1018-20. doi: 10.1259/bjr.71.850.10211060. PMID: 10211060. (Year: 1998).

(Continued)

*Primary Examiner* — Amy R Sipp
(74) *Attorney, Agent, or Firm* — Soody Tronson; STLG Law Firm

(57) ABSTRACT

Embodiments of claimed subject matter are directed to a malleable and integrally illuminated surgical retractor. In an embodiment, a malleable steel strip, having a thickness approximately in the range of 0.5-1.0 mm, may form a substrate. An elastically deformable layer, such as a polymeric layer, may be secured to the malleable steel strip. One or more meandering conductive lines, spiral conductors, or conductive inks, which may elongate and/or compress during bending of the substrate, may be secured to the TPU layer. The one or more meandering conductive lines, spiral conductors, or conductive inks may operate to couple current from an electronics module to one or more malleable illumination sources comprising, for example, an organic light-emitting diode (OLED).

13 Claims, 5 Drawing Sheets

Related U.S. Application Data continuation of application No. 15/642,426, filed on Jul. 6, 2017, now Pat. No. 10,420,539.

(60) Provisional application No. 62/457,962, filed on Feb. 12, 2017.

(58) Field of Classification Search
USPC ................ 600/206, 245, 209, 215, 223, 241
See application file for complete search history.

(56) References Cited

U.S. PATENT DOCUMENTS

| | | | | |
|---|---|---|---|---|
| 9,378,450 | B1 * | 6/2016 | Mei | G06K 19/07722 |
| 10,420,539 | B2 * | 9/2019 | Duggal | A61B 90/30 |
| 2001/0008961 | A1 * | 7/2001 | Hecker | A61M 5/46 604/521 |
| 2002/0121709 | A1 | 9/2002 | Matsuki | |
| 2003/0095781 | A1 | 5/2003 | Williams | |
| 2003/0184219 | A1 * | 10/2003 | Duggal | H10K 50/854 313/506 |
| 2004/0010208 | A1 * | 1/2004 | Ayad | A61B 5/291 600/587 |
| 2007/0017136 | A1 * | 1/2007 | Mosher, Jr. | G06K 19/0716 40/633 |
| 2007/0060795 | A1 | 3/2007 | Vayser | |
| 2007/0217200 | A1 | 9/2007 | Yang | |
| 2008/0081952 | A1 * | 4/2008 | Josephberg | A61B 17/0231 600/245 |
| 2011/0112373 | A1 | 5/2011 | Ainsworth | |
| 2014/0249520 | A1 | 9/2014 | Ghaffari | |
| 2014/0275792 | A1 * | 9/2014 | Hawkins | A61B 90/06 600/245 |
| 2016/0008088 | A1 | 1/2016 | Vayser | |

OTHER PUBLICATIONS

Kang, H.; Rajendran, S.H.; Jung, J.P. Low Melting Temperature Sn—Bi Solder: Effect of Alloying and Nanoparticle Addition on the Microstructural, Thermal, Interfacial Bonding, and Mechanical Characteristics. Metals 2021, 11, 364. https://doi.org/10.3390/met11020364 (Year: 2021).

Opdahl P.J. (2016) Anisotropic Conductive Adhesives. In: Chen J., Cranton W., Fihn M. (eds) Handbook of Visual Display Technology. Springer, Berlin, Heidelberg, https://doi.org/10.1007/978-3-642-35947-7_65-3 (Year: 2016).

* cited by examiner

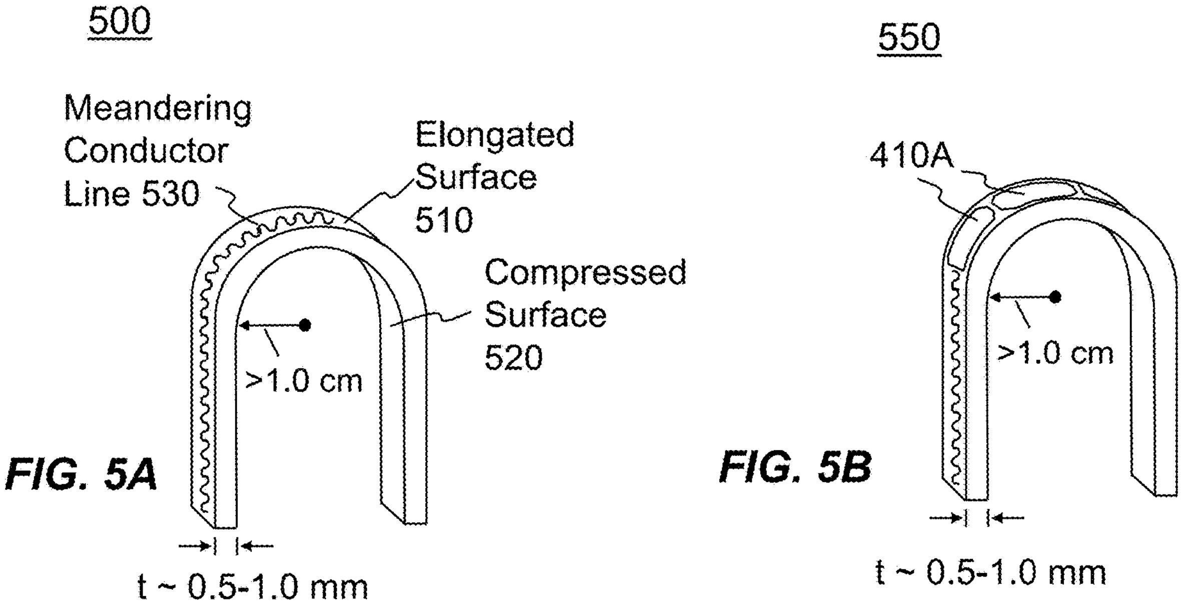
FIG. 5A
FIG. 5B
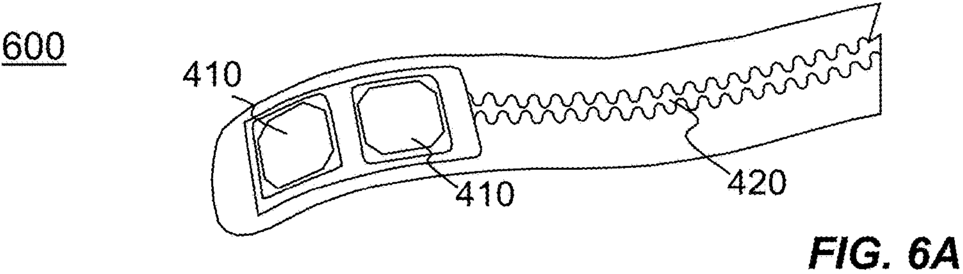
FIG. 6A
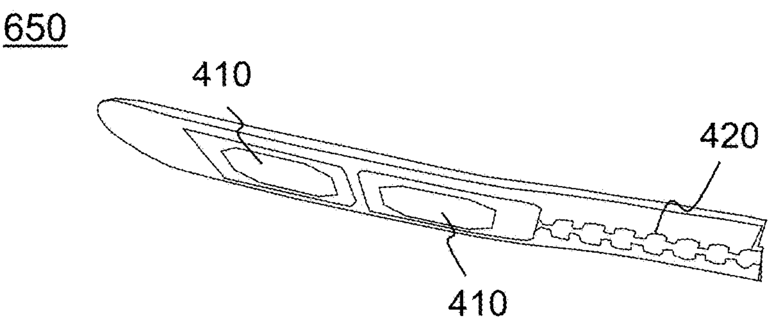
FIG. 6B

700
L
W
T
710

720

732
730
734

730
720
710

730
740
744
742

750
750
730
756
752

755

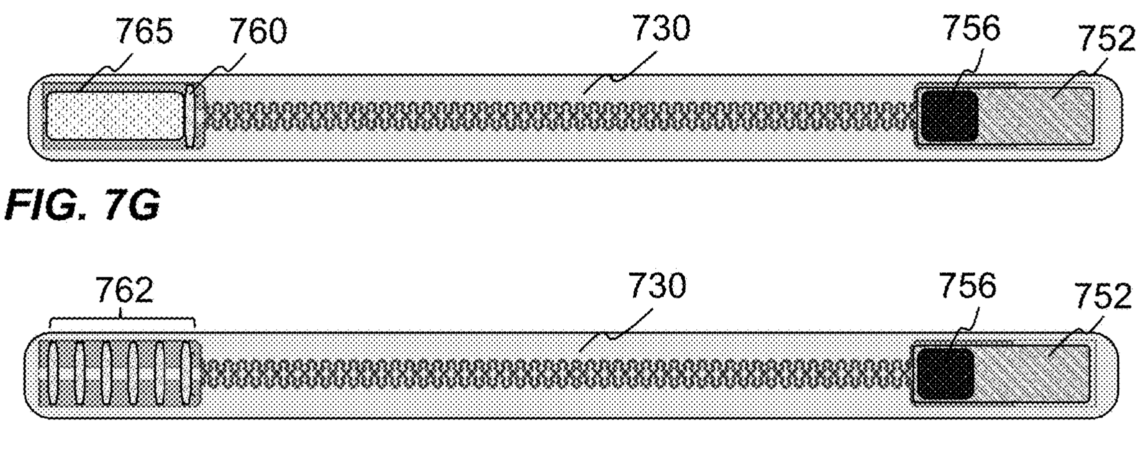
FIG. 7G
FIG. 7H
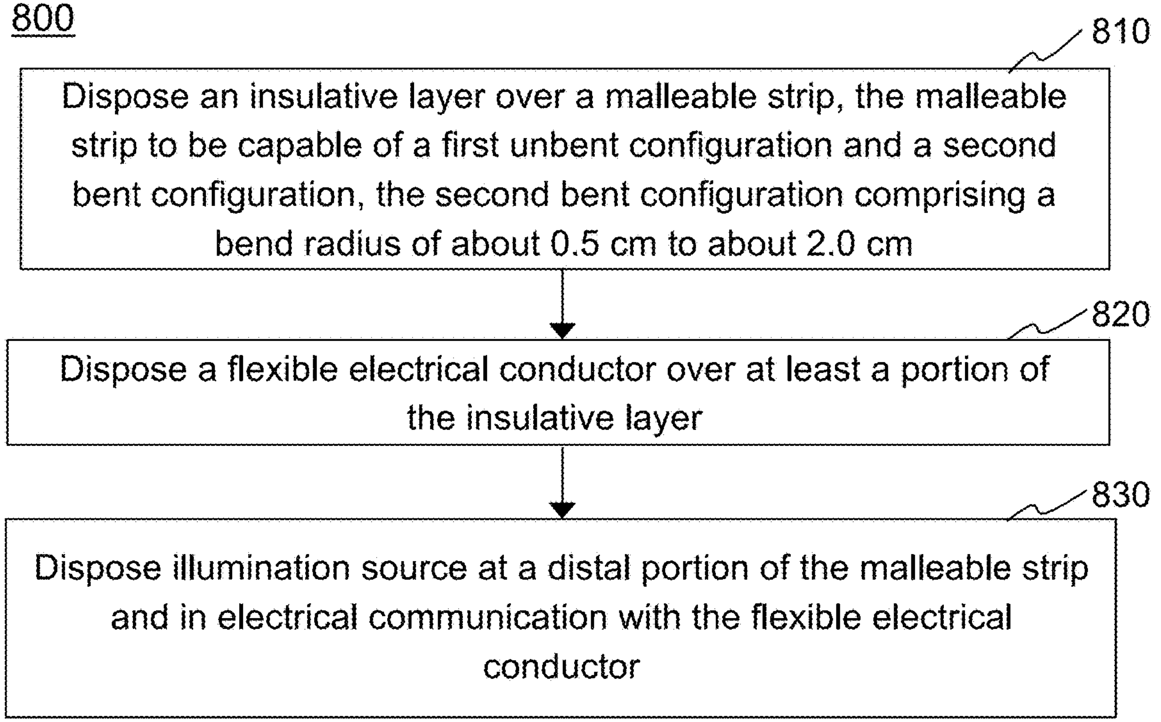
FIG. 8

MALLEABLE RETRACTOR

CROSS REFERENCE TO RELATED APPLICATIONS

This application is a continuation of U.S. patent application Ser. No. 16/540,833, filed Aug. 14, 2019, which is a continuation of U.S. patent application Ser. No. 15/642,426, filed Jul. 6, 2017, now U.S. Pat. No. 10,420,539, which is expressly incorporated in its entirety herein by reference.

BACKGROUND

1. Field

This disclosure relates generally to the field of surgical devices and, more particularly, to one or more approaches toward directing illumination from a surgical device towards a surgical area of interest.

2. Information

While performing a surgical procedure, a surgeon may utilize a retractor, which may allow the surgeon to draw lateral and deep layers of tissue away from underlying features and/or structures. Responsive to the drawing or retracting of lateral and deep layers away from underlying features, a surgeon may focus his or her attention on repair, manipulation, and/or replacement of body organs, and/or other anatomical structures including, but not limited to, soft tissue, nerve, venous, arterial, tendinous, and bony structures, and/or may perform numerous other surgical procedures.

However, at times, a surgical instrument and/or other operating room equipment may give rise to shadowing of light from an overhead source intended to illuminate a surgical area of interest. Other sources of blockage or limiting of overhead light may include the surgeon's head, body, and/or hands, for example, and/or one or more body parts of an assistant. Further, other instrumentation in and around the surgical field may obscure the surgical field from the surgeon's view. Accordingly, a surgeon may be required to reposition surgical instruments and/or overhead lighting or may be required to wear a headlamp so as to provide a clear and/or illuminated view of a surgical area of interest.

One approach toward achieving better control over illumination of a surgical area of interest may include use of fiber-optic conduits in a surgical retractor so as to provide local illumination of, for example, a surgical field (or portion thereof). However, fiber-optics-based illuminated surgical retractors may be attached to cables, such as electrical and/or fiber-optic cables, which may impede a surgeon's freedom to orient a surgical retractor into a desired position. Additionally, fiber-optics-based retractors may direct illumination predominately along the longer dimension of a surgical retractor, without providing sufficient illumination directly beneath the retractor. Further, fiber-optics-based retractors may comprise rigid structures that may be unable to conform to a curvature dictated by a structure or feature within a surgical area of interest so as to permit illumination within, for example, small openings of a human or animal body.

SUMMARY OF DISCLOSURE

The present invention is directed to illuminated malleable surgical retractors, including integrally-illuminated malleable surgical retractors, and methods for making and using the same.

In an embodiment, a surgical retractor embodying features of the present invention, comprises a malleable substrate, such as a strip having a proximal end and a distal with a distal portion. The malleable strip being capable of a first unbent configuration and a second bent configuration having a bend radius of less than about 2.0 cm. However, in an embodiment the bend radius may be less than about 1.0 cm.

The malleable strip may comprise shapeable steel, stainless steel, a steel alloy, aluminum, titanium, plastic, ceramic, fluidized metal, or any combination thereof. In some embodiments, the substrate comprises a nominal thickness approximately in the range of about 0.5 to about 1.0 mm.

The retractor may further comprise an insulative layer, such as an elastically deformable layer, which may comprise a polymeric layer, disposed over the malleable strip and a planar illumination source disposed over the insulative layer at the distal portion of the strip. In embodiments, the insulative layer is a stretchable layer, such as an elastically deformable polymeric layer, and/or may comprise silicone, thermoplastic polyurethane (TPU), polyvinyl chloride (PVC), synthetic polymer, transparent ceramic material, transparent metal, flexible glass, bio-inert acrylonitrile-butadiene-styrene (ABS), or combinations thereof. The insulative material, is preferably selected so as to permit, in operation, the bending of the retractor without separation of the insulative material from the malleable strip.

The planar illumination source may comprise one or more light-emitting diodes (LEDs), organic light-emitting diodes (OLEDs), bioluminescent sources, or any other type of light-emitting electronic component, which may serve to illuminate a surgical field while restricting illumination of surrounding areas.

In some embodiments, a combined thickness of the malleable strip, the insulative layer, and the planar illumination source is less than about 2.0 mm.

In an embodiment, one or more light-adjusting layers may be disposed over the planar illumination source. The light adjusting layer may comprise one or more light-diffusing layers or a light-scattering layer, or a combination thereof.

In exemplary embodiments, the light-diffusing layer may comprise a foil that operates to redirect a fraction (e.g., approximately in the range of 3.0%-8.0%) of light generated by the one or more planar illumination sources. Redirected light may be dispersed over a wide viewing angle, which may permit a more widely-dispersed distribution of light from one or more of planar illumination sources. In exemplary embodiments, a light-diffusing layer may comprise phosphorus particles, organic fluorescent dye, titanium dioxide particles, or may comprise any other scattering media, and claimed subject matter is not limited in this respect.

In an embodiment the illumination source (e.g., LED) may be coupled to an optical waveguide comprising a scattering material, such as phosphorus particles, titanium dioxide particles, organic fluorescent dye, or other scattering media, which may function to redirect incoming light from the illumination sources towards a surgical field of interest.

The surgical retractor may further comprise, at a handle portion disposed at a proximal end of the strip, opposite the distal end of the flexible strip, a flexible charge storage module or a flexible charge dispensing module, or a combination thereof. The flexible charge storage module or the flexible charge dispensing module, or the combination thereof, utilizing any one of suitable charge storage technologies such as layered capacitors, fuel cells, electrochemical storage, and/or inductively charged energy storage components.

In an embodiment, the malleable surgical retractor may further comprise an electrical conductor disposed over the insulative layer to convey an electrical current from the flexible charge storage/charge dispensing module to the planar illumination source. The electrical conductor may comprise a flexible elongate conductive element having a first longitudinal dimension and a second longitudinal dimension being up to at least about 120.0% of the first longitudinal dimension. The electrical conductor may further comprise conductive pads disposed at one or more of proximal and distal end portions of the flexible elongate conductive element, wherein the conductive pads disposed at the one or more of the proximal and distal end portions are in electrical communication with each other.

The flexible elongate conductive element may comprise a meandering conductive element, a spiral-shaped element or a conductive ink, or any combination thereof.

The flexible elongate conductive element may be disposed over or directly on the insulative material and may be secured by any suitable means, and may be for example disposed, affixed, adhered, overlaid, deposited (e.g., vapor deposition).

In an embodiment, a control element in electrical communication with the flexible charge storage/charge dispensing module may be disposed at the proximal end of the strip to regulate the electrical power conveyed from a charge storage/charge dispensing module to the planar illumination source.

Methods embodying features of the present invention for making malleable retractors embodying features of the present invention, may comprise disposing an insulative layer on or over a malleable strip having a proximal portion and a distal portion. The malleable retractor may be capable of comprising a first unbent configuration and a second bent configuration having a bend radius of about 0.75 cm to about 2.0 cm, disposing an electrical conductor over at least a portion of the insulative layer, and disposing an illumination source at the distal portion of the malleable strip and in electrical communication with the flexible conductor.

The method may further comprise disposing a light-adjusting layer over the illumination source. The method may further comprise disposing a flexible charge storage module, a flexible charge dispensing module, or a combination thereof, at a proximal portion of a malleable strip. An electrical conductor to convey current from the flexible charge storage module, the flexible charge dispensing module, or the combination thereof to the illumination source may comprise a flexible elongate conductive element comprising a meandering conductive line, a spiral-shaped conductor, a conductive ink, or a combination thereof. The flexible elongate conductive element has a first longitudinal dimension and a second longitudinal dimension comprising up to at least 120.0% of the first dimension.

In an embodiment for implementing the method, the illumination source may comprise one or more organic light-emitting diodes, one or more light-emitting diodes, one or more bio-luminescent sources, or any combination thereof.

It should be understood that the aforementioned implementations are merely example implementations, and that claimed subject matter is not necessarily limited to any particular aspect of these example implementations.

BRIEF DESCRIPTION OF DRAWINGS

Claimed subject matter is particularly pointed out and distinctly claimed in the concluding portion of the specification. However, both as to organization and/or method of operation, together with objects, features, and/or advantages thereof, it may best be understood by reference to the following detailed description if read with the accompanying drawings in which:

FIGS. 5A-5B are illustrations showing extension and compression of surfaces brought about by bending a malleable and integrally-illuminated a surgical retractor according to an embodiment;

FIGS. 6A-6B are illustrations showing portions of a malleable and integrally-illuminated a surgical retractor according to embodiments;

FIGS. 7A-7H is an illustration showing layers of a malleable and integrally-illuminated surgical retractor according to embodiments; and FIG. 8 is a flowchart for a method of constructing a malleable and integrally-illuminated surgical retractor according to an embodiment.

Figure 1:
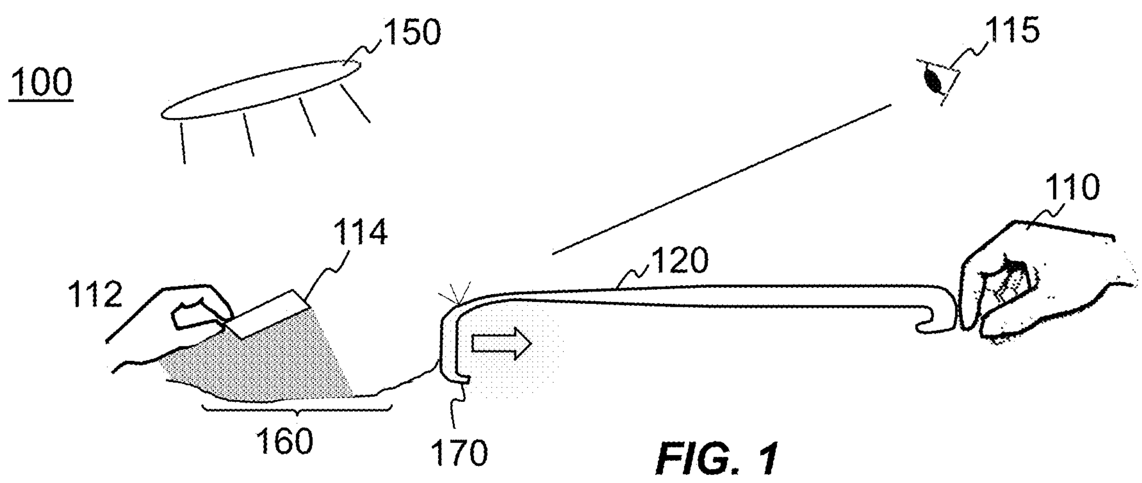
FIG. 1 is an illustration of a surgical retractor in use during a surgical procedure.

Reference is made in the following detailed description to accompanying drawings, which form a part hereof, wherein like numerals may designate like parts throughout to indicate corresponding and/or analogous components. It will be appreciated that components illustrated in the figures have not necessarily been drawn to scale, such as for simplicity and/or clarity of illustration. For example, dimensions of some components may be exaggerated relative to other components. Further, it is to be understood that other embodiments may be utilized. Furthermore, structural and/or other changes may be made without departing from claimed subject matter. It should also be noted that directions and/or references, for example, up, down, top, bottom, and so on, may be used to facilitate discussion of drawings and/or are not intended to restrict application of claimed subject matter. Therefore, the following detailed description is not to be taken to limit claimed subject matter and/or equivalents.

DETAILED DESCRIPTION

Reference throughout this specification to "one example," "one feature," "one embodiment," "an example," "a feature," or "an embodiment" means that a particular feature, structure, or characteristic described in connection with the feature, example or embodiment is included in at least one feature, example or embodiment of claimed subject matter. Thus, appearances of the phrase "in one example," "an example," "in one feature," a feature," "an embodiment," or "in one embodiment" in various places throughout this specification are not necessarily all referring to the same feature, example, or embodiment. Furthermore, particular features, structures, or characteristics may be combined in one or more examples, features, or embodiments.

As previously described, a surgeon may utilize a surgical retractor to draw or pull away lateral and deep layers of tissue to expose one or more underlying features of, for example, a human or animal body. Retraction of lateral and deep layers may permit the surgeon and/or other medical personnel to perform surgical procedures, for example, deep within a human or animal body. However, on occasion, polished, sterilized surgical instruments, such as a retractor, may produce glare from overhead illumination sources. Responsive to observing such glare, a surgeon may be required to shift his or her position and/or reposition one or more surgical instruments. Such adjustment of a surgeon's position and/or repositioning of surgical instruments may reduce a surgeon's efficiency, for example, and may increase the time required to complete a surgical procedure, which may lead to potentially increased postoperative complications associated with prolonged operating times, for example, or may render a procedure more technically difficult.

In some instances, such as during very precise surgical procedures involving fine structures of the human body, an amount of overhead light illuminating a surgical area may be increased so as to permit the surgeon to clearly view the surgical area and to improve surgical safety by, for example, reducing surgeon error, such as inadvertently cutting, suturing, and/or damaging vital anatomical structures. However, in these instances, and others, such an increase in ambient and/or overhead illumination may exacerbate glare produced by surgical instruments or may over illuminate areas surrounding the surgical incision. Presence of additional glare may, in turn, require additional repositioning of one or more surgical instruments, for example, or dimming the lights below acceptable levels to reduce glare, for example.

In embodiments, use of a malleable and integrally illuminated surgical retractor may reduce a need for ambient surgical lighting, such as overhead lighting, thus reducing or eliminating glare introduced by overhead and/or ambient surgical lighting as well as reducing shadowing of a surgical area of interest. Such reduction or elimination of glare entirely, may, for example, reduce annoying eyestrain experienced by a surgeon, as well as reduce the need to reposition surgical instruments during surgical procedures, for example. Accordingly, embodiments may bring about a reduction in the time required to perform a surgical procedure as well as an increase in a surgeon's comfort and efficiency.

In embodiments, a bend radius may bring about a capability to form a tightly curved retractor, which may thereby allow a surgeon to operate utilizing smaller incisions. Additionally, a tightly curved retractor may allow the surgeon to "toe-in" a retractor, in which the angular position of the retractor may be adjusted so as to penetrate further into tissue nearby the surgical field of interest. Further, a malleable surgical retractor may permit a surgeon to bend, curve, or bow the retractor in multiple places, thereby permitting the retractor to perform within tight confines.

In addition, use of a malleable and integrally illuminated surgical retractor may permit a surgeon to conform the retractor to accord to a complex curvature dictated by an anatomical structure or feature to permit illumination within, for example, small openings of a human or animal body. In one instance, to perform surgery involving areas behind (e.g., posterior to) the human eye may require a retractor to bend around processes of the zygomatic bone of the human skull so that regions posterior to the human eyeball may be viewed. In other instances involving thoracic surgery, it may be advantageous for a surgeon to position a retractor in between individual human ribs. In these instances, and potentially many others, an integrally illuminated surgical retractor, comprising a high degree of flexibility, may be particularly advantageous to surgeons, patients, and others.

A malleable and integrally illuminated surgical retractor may permit precise illumination of particular structures within tightly confined surgical areas of interest in addition to reducing glare introduced by reflections from various overhead and/or ambient surgical lighting systems. In an example embodiment, an illuminating surgical retractor may comprise light-emitting diodes (LEDs), organic light-emitting diodes (OLEDs), bioluminescent sources, or may comprise any other type of light-emitting electronic component, which may serve to illuminate a surgical field while restricting illumination of surrounding areas. In embodiments, an illuminating surgical retractor may comprise a single control element, positioned near a handle or a grip of the device, which may permit a surgeon to control intensity of light from, for example, LEDs and/or OLEDs.

Flexibility of an integrally illuminated surgical retractor may be made possible through the use of one or more meandering conductive lines secured or disposed, such as via depositing, affixing, or adhering, for example, to a surface of the retractor comprising a stainless steel strip. In embodiments, a meandering conductive material may comprise an elastic property that permits repeated expansion and contraction while retaining conductive properties. Additionally, by utilizing LEDs and/or OLEDs, an electric current (such as required to provide primary power to one or more LEDs and/or OLEDs) may be maintained at a relatively low level, thereby requiring only limited current be conveyed by one or more meandering conductive lines. In addition, at least partially due to the use of substantially planar OLEDs and planar meandering conductive lines, a malleable and integrally illuminated surgical retractor may comprise a thickness approximately in the range of 1.0 mm.

FIG. 1 is an illustration of a surgical retractor in use during a surgical procedure. As shown in FIG. 1, surgeon's hand 110 may indicate use of a surgeon or medical assistant, for example, operating surgical retractor 120, such as during a surgical procedure to draw or retract one or more layers of tissue. Responsive to retraction of lateral and deep layers of tissue, for example, using blade portion 170, surgical field 160 may be exposed, for example, to be viewed by a surgeon, represented by eye 115. However, in the embodiment of FIG. 1, overhead light 150 may bring about glare, for example, produced by polished surfaces of the surgical retractor 120. Such glare may represent a nuisance to a surgeon and/or other medical personnel present in an operating room. In addition, surgical instrument 114, which may comprise a clamp, a pair of forceps, or other surgical utensil, may represent an additional source of nuisance glare to the surgeon and/or other personnel in an operating room, for example. In addition to sources of glare produced by polished surgical instruments, hands or other limbs of operating room personnel may bring about shadowing of portions of the surgical field. For example, FIG. 1 shows shadowing by a limb, such as hand 112, of an assistant, for example, which may further occlude or hinder a surgeon's clear vision of surgical field, such as surgical field 160.

Figure 2:
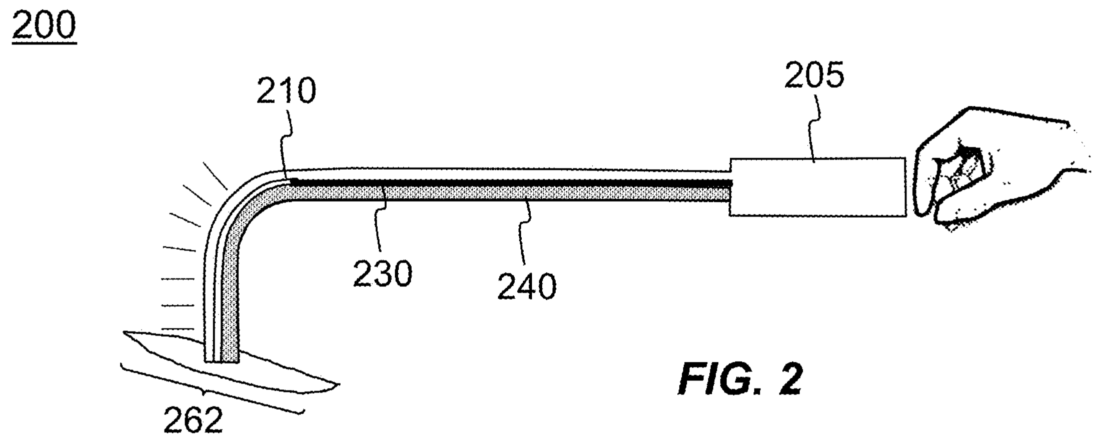
FIG. 2 is an illustration of a malleable and integrally-illuminated surgical retractor according to an embodiment.

FIG. 2 is an illustration of a malleable and integrally illuminated surgical retractor according to an embodiment 200. In FIG. 2, an end portion may comprise illumination source 210, which may bring about illumination of surgical field 262 in an absence of overhead lights, such as overhead light 150 of FIG. 1. In embodiment 200, an end portion of the surgical retractor, opposite handle portion 205, may comprise an OLED, solid-state LED, or may comprise an array of solid-state LEDs and or OLEDs. The end portion of the surgical retractor may additionally comprise a light diffuser, or other type of light-adjusting element, disposed over the illumination source, which may operate to increase uniformity and/or to increase scattering of distributed light emanating from the LED and/or OLED illumination source. In particular embodiments, flexible conductor 230, which may comprise a meandering or spiral-shaped conductor, described further herein, may provide electrical power to illumination source 210 while permitting the malleable and integrally illuminated surgical retractor to be formed or bent into virtually any shape. Malleable substrate 240, to which flexible conductor 230 and illumination source 210 may be secured, such as via depositing, adhering, affixing, and so forth, may comprise a shapeable plastic or a thin strip of stainless steel, steel alloy, aluminum, titanium, or other metal or metal alloy, or combinations of metals to form a task-specific material having a thickness approximately in the range of 0.5-1.0 mm, for example. In other embodiments, malleable substrate may comprise a plastic, ceramic, elastomeric material, and/or a fluidized metal, for example. In embodiments, malleable substrate 240 may permit flexing of the surgical retractor to a bend radius of as little as 1.0 cm, for example. Aspects of other embodiments of a surgical retractor that accord with embodiment 200 are explained further herein.

Figure 3:
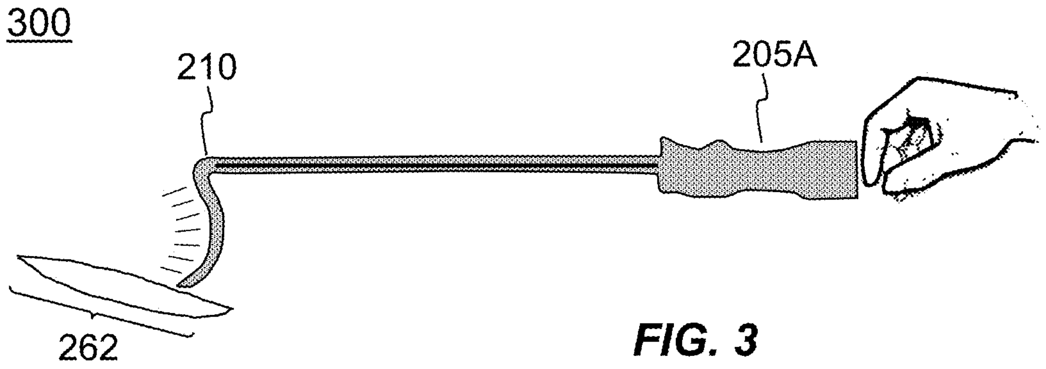
FIG. 3 is an illustration of a malleable and integrally-illuminated surgical retractor showing flexibility of an illuminating end portion and a conformal handgrip according to an embodiment.

FIG. 3 is an illustration of a malleable and integrally illuminated surgical retractor showing flexibility of an illuminating end portion and a conformal handgrip according to an embodiment 300. Accordingly, as shown in FIG. 3, handle portion 205A may be formed or molded to comprise features to mate with the shape of a human hand, so as to permit a surgeon to comfortably grip handle portion 205 during surgical procedures. At an opposite end of handle portion 205A, illumination source 210 is shown as being malleable, thereby permitting shaping of an end portion of handle 205 to permit illumination of tight crevices, such as crevice 262, within a human or animal body, for example, or to bend around anatomical structures during surgical procedures.

Figure 4:
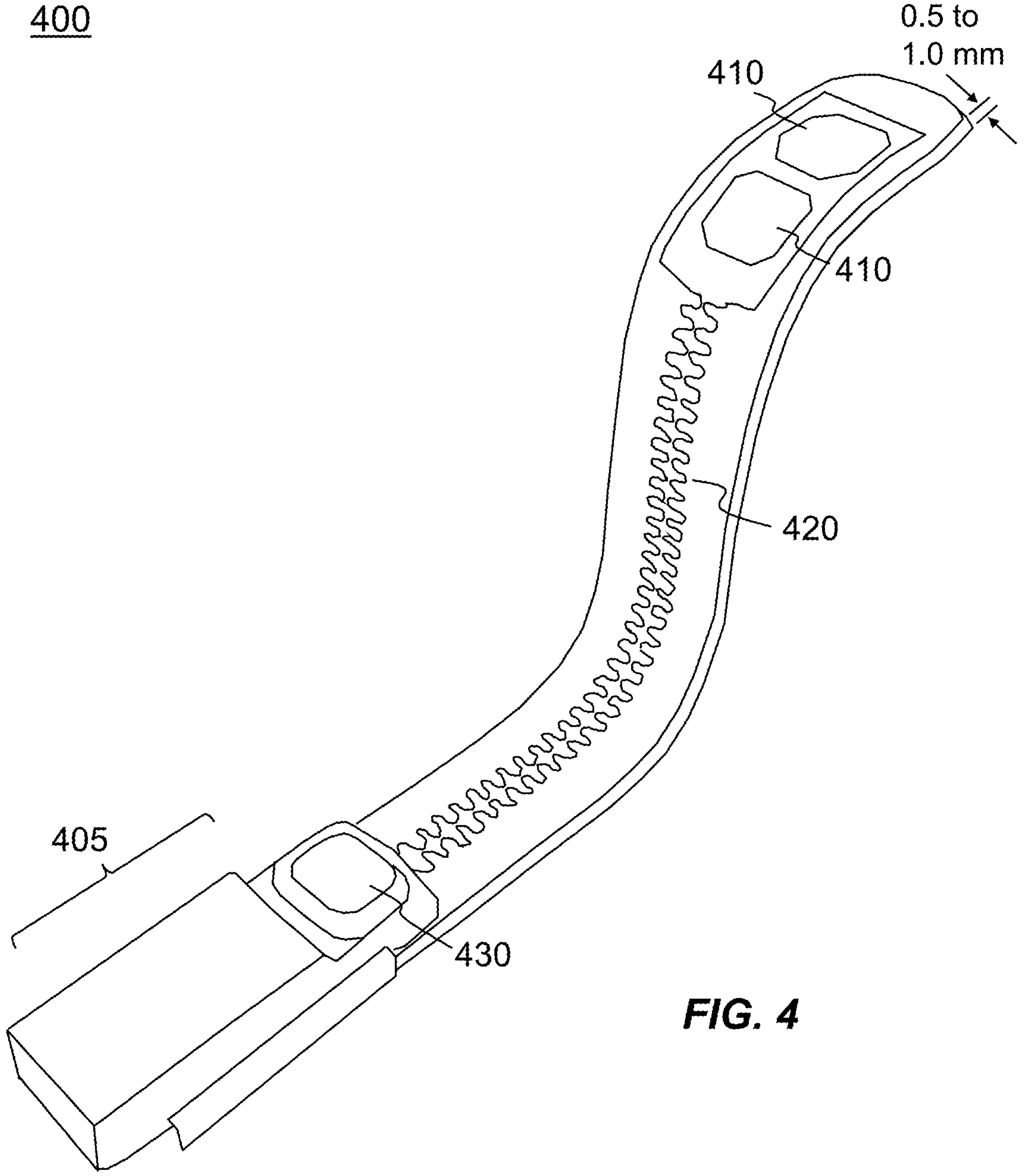
FIG. 4 is a perspective view of a malleable and integrally-illuminated surgical retractor according to an embodiment.

FIG. 4 is a perspective view of a malleable and integrally illuminated surgical retractor according to an embodiment 400. In embodiment 400, a handle portion 405 comprises a control element 430, which may permit a surgeon, for example, to control the on/off state or to otherwise control electrical powered delivered to one or more of illumination sources 410. For example, in a particular embodiment, depressing control element 430 may activate one or more of illumination sources 410 at a first level of brightness. Depressing control element 430 a second time may activate illumination sources 410 at a second level of brightness. Depressing control element 430 additional times may result in further incremental steps in the brightness of illumination sources 410. In a particular embodiment, responsive to illumination sources 410 attaining a relatively high level of brightness, depressing control element an additional time may return illumination sources 410 to a deactivated (e.g., "off") state.

In the embodiment of FIG. 4, a malleable and integrally illuminated surgical retractor may comprise a shapeable plastic or a thin metallic strip comprising stainless steel or any other metal/metal alloy, comprising a thickness approximately in the range of 0.5-1.0 mm, for example. In embodiments, a layer of stretchable insulative material, such as silicone, thermoplastic polyurethane (TPU), or any type of elastically deformable material (which may comprise a polymeric layer, for example), may be formed or fabricated on or over the malleable strip so as to permit the bending of the retractor without separation of the insulative material from the malleable strip. In this context, the term "elastically deformable material," such as may be formed or fabricated on or over the malleable strip is defined as a material comprising a substantial portion of a polymeric elastically deformable material, such as silicone, TPU, polyvinyl chloride (PVC), synthetic polymer, transparent ceramic material, transparent metal, flexible glass, bio-inert acrylonitrile-butadiene-styrene (ABS), or combinations thereof. Meandering conductor line 420, which may be disposed or deposited over the stretchable insulative material, may provide an electrical connection between control element 430 and illumination sources 410 while the malleable and integrally-illuminated surgical retractor of embodiment 400 is undergoing bending or flexion, such as during surgical procedures.

In one example, as shown in more detail in FIG. 5A, during bending of the retractor of embodiment 400 in a first (downward direction as shown in FIG. 4), such as from a flattened or unbent state, meandering conductor line 420 may comprise an elastic quality so as to the capable of an increase in length (e.g., elongated) of up to 20.0%. Additionally, in certain embodiments, meandering conductor line 420 may comprise a quality of even greater elasticity, such as being capable of an increase in length by greater amounts, such as 25.0%, 30.0%, or 40.0%, for example. Further, in particular embodiments, during bending of the retractor of embodiment 400 in a second (upward direction as shown in FIG. 4), such as from a flattened or unbent state, meandering conductor line 420 may be capable of being decreased in length (e.g., compressed) up to 20.0%. Additionally, in certain embodiments, meandering conductor line 420 may be capable of being compressed in length by greater amounts, such as 25.0%, 30.0%, or 40.0%, for example. It should be noted that meandering conductor line 420 may be capable of greater amounts of elongation/compression, and claimed subject matter is not limited in this respect.

FIG. 5 is an illustration showing extension and compression of surfaces brought about by bending a portion of malleable and integrally illuminated a surgical retractor according to embodiment 500. As shown in FIG. 5A, meandering conductor line 530 is disposed or deposited on a surface 510 of a portion of a surgical retractor. Thus, responsive to bending or shaping of a portion of a malleable and integrally-illuminated surgical retractor, such as to comprise a bend radius of, for example, less than 1.0 cm, meandering conductor line 530 may undergo stretching or elongation, relative to a flattened or unbent state. In addition, during bending or shaping of the portion of a malleable and integrally illuminated retractor, surface 520 may undergo compression relative to a flattened or unbent state. In embodiments, a portion of the retractor may be bent or shaped to comprise a different bend radius, such as, for example, less than 1.0 cm, such as 0.75 cm, or may be bent or shaped to comprise a bend radius of greater than 1.0 cm, such as 2.0 cm, 3.0 cm, etc. In embodiments, if a portion of a surgical retractor is shaped so as to comprise a bend radius of, for example, 1.0 cm, elongation of a meandering conductor line, such as meandering conductor line 420, for example, of approximately 20.0% may occur. In other embodiments, if a portion of a surgical retractor is shaped so as to comprise a bend radius of 0.75 cm (7.5 mm) elongation of a meandering conductor line, such as meandering conductor line 420, for example, of approximately 25.0% may occur. However, claimed subject matter is not limited in this respect.

Responsive to bending or shaping of a portion of a malleable and integrally illuminated surgical retractor of embodiment 500 in a direction opposite the direction shown in FIG. 5A, meandering conductor line 530 may undergo compression of, for example, 20.0%. In such an embodiment, meandering conductor line 530 may be located at compression surface 520 of FIG. 5A. Thus, it can be appreciated that a malleable and integrally-illuminated retractor may accommodate bending in a first direction, as shown in FIG. 5A, as well as bending in a direction opposite shown in FIG. 5A, which may bring about elongation or contraction of meandering conductor line 530 by an amount of, for example, ±20.0%. However, it can be appreciated that other embodiments may permit elongation or contraction of a meandering conductor line by, for example, ±25.0%, ±30.0%, etc. Additionally, although only a single meandering conductor line 530 has been illustrated in FIG. 5A, it is contemplated that particular embodiments of a malleable and integrally-illuminated retractor may utilize two meandering conductive lines, such as shown in embodiment 400 of FIG. 4.

FIG. 5B is an illustration showing extension and compression of surfaces brought about by bending a portion of malleable and integrally illuminated a surgical retractor according to embodiment 550. In the embodiment of FIG. 5B, illumination sources 410A, which may be similar in function and construction to illumination sources 410, are shown as adhered to an outer surface of a malleable retractor, which may be elongated or compressed by an amount approximately in the range of 20.0%, 30.0%, and so forth when bent in a first direction. In a manner that accords with that of FIG. 5A, when the malleable retractor of FIG. 5B is bent in an opposite direction, illumination sources 410A may contract by amount approximately in the range of 20.0%, 30.0%, etc. It should be noted that claimed subject matter is intended to embrace malleable, stretchable illumination sources, such as OLEDs, as well as other types of illumination sources.

In particular embodiments, one or more meandering conductive lines of a malleable retractor may comprise an isotropic conductive adhesive, an anisotropic conductive adhesive, or other type of low-temperature curing/melting conductive material. For example, a meandering conductor line may comprise a lead-free solder paste alloy of tin and bismuth (SnBi) having a melting point approximately in the range of, for example, 120° C.-150° C. In other embodiments, one or more meandering conductive lines of a malleable retractor may comprise a spiral-shaped wire to permit elongation and compression as the malleable retractor is bent during surgical procedures. In additional embodiments, one or more meandering conductive lines may comprise a conductive ink that may be printed on or over an insulating layer. It should be noted that claimed subject matter is intended to embrace all approaches toward achieving a conductive interconnection between end portions of a malleable surgical retractor, and claimed subject matter is not limited in this regard.

FIGS. 6A and 6B are illustrations showing portions of a malleable and integrally illuminated a surgical retractor according to embodiments 600 and 650. Embodiment 600 shows illumination sources 410 coupled to meandering conductor line 420 while the portion of the retractor is only slightly bent. Embodiment 650 shows illumination sources 410 coupled to meandering conductor line 420 while the portion of the retractor is maintained in a relatively flat or unbent state.

Figures 7A, 7B, 7C, 7D, 7E, 7F:
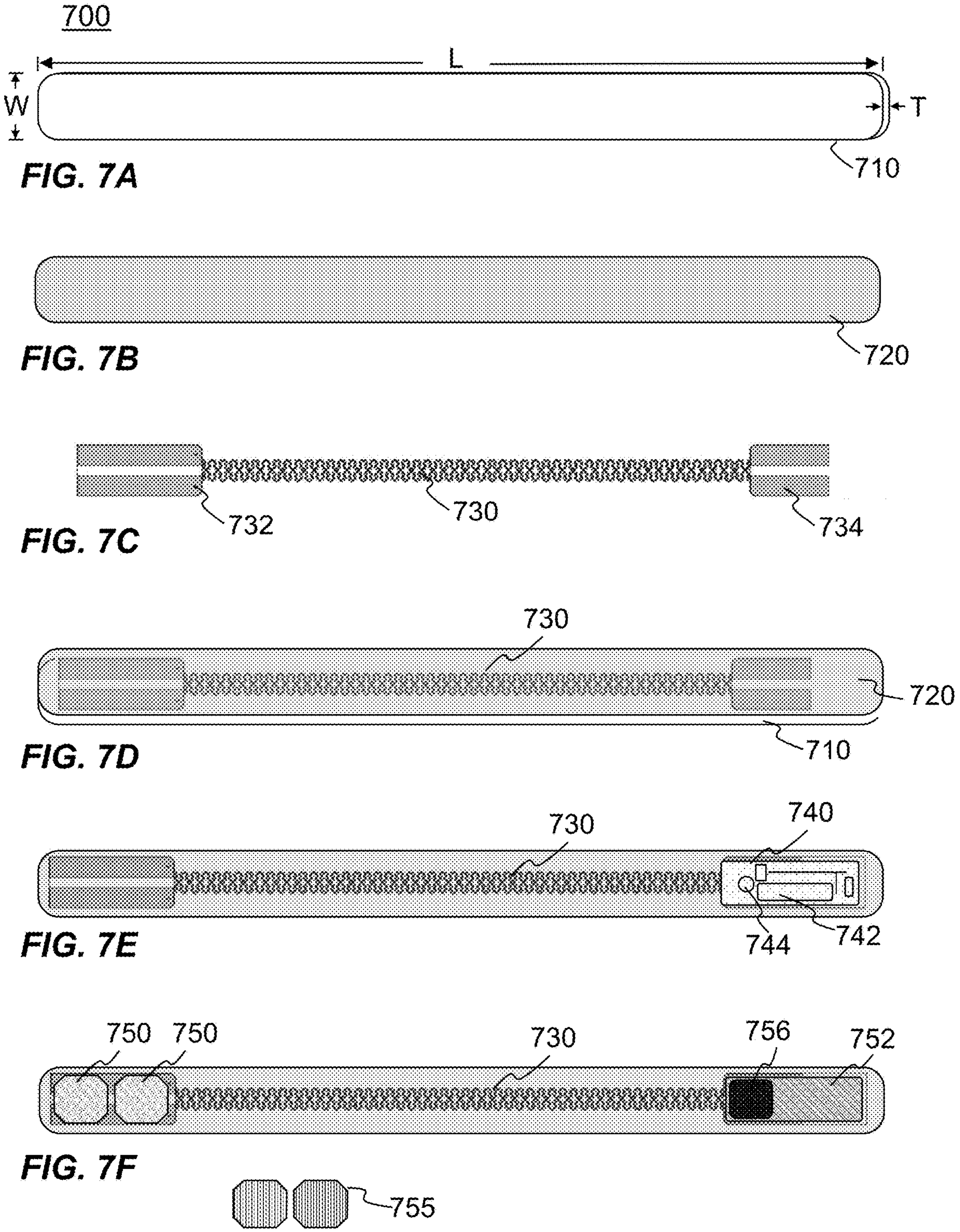

FIGS. 7A-7F, is an illustration showing layers of a malleable and integrally-illuminated surgical retractor according to an embodiment 700. In particular embodiments, layers of the malleable and integrally-illuminated surgical retractor may cooperate to form a first unbent configuration and a second bent configuration having a bend radius of less than about 2.0 cm. In FIG. 7A, stainless steel strip 710, having a length (L) approximately in the range of 25.0 cm-40.0 cm, a width of approximately in the range of 2.0 cm-5.0 cm, and a thickness (T) approximately in the range of 0.5 mm-1.0 mm, may be utilized to form a malleable substrate for an integrally-illuminated surgical retractor. In a prototype embodiment, a stainless steel strip, such as stainless steel strip 710, having a thickness of approximately 1.0 mm has been found to be capable of bending to a radius of approximately 2.0 cm while involving only average force, such as between about 1.0 Newton and 50.0 Newton, to bring about such bending. In addition, an approximately 1.0 mm thick stainless steel strip, such as that of the prototype embodiment, has been found to comprise sufficient rigidity so as to maintain a shape during typical surgical procedures, such as laterally drawing layers of soft tissue away from an area of an incision, pushing tissue edges apart from one another, separating layers of tissue from one another, and holding repositioned layers of soft tissue in place for typical durations of surgical sub-procedures, for example.

It should be noted that for other surgical procedures, a malleable and integrally-illuminated surgical retractor may comprise a malleable strip, such as stainless steel strip 710, having a thickness greater than approximately 1.0 mm (e.g., 1.5 mm, 2.0 mm, etc.) so as to comprise above average rigidity. Procedures that may utilize and benefit from a surgical retractor having increased rigidity may include separation of cartilage from bone, for example. In particular embodiments, stainless steel strip 710 may comprise a bulk modulus approximately in the range of 150 GPa to 250 GPa, and claimed subject matter is not limited in this respect.

FIG. 7B shows a thin layer of insulative layer (720), which may be applied on or over stainless steel strip 710. In embodiments, insulative layer may comprise TPU or other insulative, stretchable material that may remain secured (e.g., disposed, affixed, adhered, overlaid, deposited) to stainless steel strip 710 as the surgical retractor is bent, for example, during surgical procedures. In embodiments, insulative layer 720, which may comprise TPU, for example, may comprise a thickness approximately in the range of 0.1 mm-0.3 mm. In embodiments, thickness of an insulative layer may be selected to provide a suitable insulator between a meandering line conductor, a conductive ink, or a spiral-shaped conductor disposed, affixed, or deposited on an insulative layer and an underlying stainless steel substrate. However, in other embodiments, an insulative layer may comprise a thickness less than 0.1 mm or may comprise a thickness greater than 0.30 mm, and claimed subject matter is not limited in this respect.

FIG. 7C shows conductive pads 732 and 734, which may comprise a thin sheet of copper, for example, electrically connected or coupled (e.g. via soldering) to each other via meandering conductive lines 730. In particular embodiments, meandering conductive lines 730, which may be similar in construction and performance as meandering conductor lines 420, may be soldered, for example, to conductive pads 732/734. FIG. 7D shows stainless steel strip 710 as lying beneath insulative layer 720 and meandering conductive line 730. FIG. 7E shows electronics module 740 disposed on conductive pads 734. Electronics module 740 may additionally comprise switch 744, which may permit a surgeon, for example, to control the on/off state of one or more illumination sources of a malleable surgical retractor. In particular embodiments, electronics module 740 may allow switch 744 to control levels of brightness of the one or more illumination sources. In certain embodiments, electronics module 740 may implement a "press and hold" feature, in which holding switch 744 in a depressed position to bring about incremental increases in illumination intensity, which may permit a surgeon to hold a surgical retractor in a steady, fixed position while adjusting illumination intensity.

In embodiments, electronics module 740 may comprise flexible battery 742, such as a battery formed from lithium ions, but may comprise a flexible charge storage module or a flexible charge dispensing module, or a combination thereof. However, in particular embodiments, flexible battery 742 may utilize any other type of charge storage technology such as layered capacitors, fuel cells, and/or inductively charged energy storage components, for example. Claimed subject matter is intended to embrace all suitable energy accumulation, energy storage, and energy dispensing technology.

FIG. 7F shows a malleable surgical retractor incorporating planar illumination sources 750, which may operate similar to illumination sources 410 of FIGS. 4, 6A, and 6B, to provide illumination of a surgical field during a surgical procedure. Cover 752 may be formed to enclose electronics module 740, and button 756 may rest on or over switch 744. Although not specifically identified in FIG. 7F, one or more exposed portions of meandering conductive lines 730 may be coated with an additional layer of insulating material, such as TPU, which may operate to seal the surgical retractor so as to be resistant to liquids encountered during surgical procedures, cleaning, and so forth.

In particular embodiments, one or more of planar illumination sources 750 may be coated with a light-adjusting layer, such as a light-diffusing layer or layer that operates as a scattering medium, such as light-adjusting layer 755. In such an embodiment, a light-adjusting layer may comprise a scattering material, such as a foil, which may operate to redirect a fraction (e.g., approximately in the range of 3.0%-8.0%) of light generated by the one or more planar illumination sources 750. Redirected light may be dispersed over a wide viewing angle, which may permit a more increased distribution of light from one or more of planar illumination sources 750. In embodiments, light-adjusting layer 755 may comprise phosphorus particles, an organic fluorescent dye, titanium dioxide particles, or may comprise any other light-scattering and/or light-adjusting media, and claimed subject matter is not limited in this respect.

In particular embodiments, light-adjusting layer 755 may perform a light-focusing operation, in which light from planar illumination sources, such as sources 750, for example, may be focused towards regions normal (e.g., in front of) illumination sources 750, so as to concentrate light towards a particular surgical area of interest. However, claimed subject matter is not limited in this respect.

FIG. 7G shows an embodiment in which a single LED 760 is shown as coupling to optical waveguide 765 such as at an angle that brings about total internal reflection within optical waveguide 765. In such an embodiment, light from LED 760 may be directed towards optical waveguide 765, which may comprise a light-adjusting material, such as a light-scattering material. In embodiments, a light-adjusting or light-scattering material may comprise, for example, phosphorus particles, titanium dioxide particles, organic fluorescent dye, or other scattering media, which may function to redirect incoming light towards a surgical field of interest.

FIG. 7H, shows an embodiment in which an array of LEDs 762 are shown as operating as an illumination source. Although shown only as an array of six LEDs, embodiments may utilize a larger number of LEDs, such as 8 LEDs, 10 LEDs, 20 LEDs, and so forth, or may utilize a smaller number of LEDs, such as 3 LEDs or 4 LEDs, for example. Additionally, although shown as an array extending in a single dimension, LEDs 762 may be arranged in a two-dimensional array, for example and claimed subject matter is not limited in this respect.

FIG. 8 is a flowchart for a method of constructing a malleable and integrally illuminated surgical retractor according to an embodiment 800. It should be noted that although blocks 810, 820, and 830 of embodiment 800 are presented in a particular order, embodiments of claimed subject matter may include blocks rearranged into a different order, or blocks of a related method comprising blocks in addition to blocks 810, 820, and 830. In the embodiment of FIG. 8, block 810 comprises disposing an insulative layer over a malleable strip, wherein the malleable strip is capable of a first unbent configuration and a second bent configuration, the second bent configuration comprising a bend radius of about 0.5 cm to about 2.0 cm. Block 820 may comprise disposing a flexible electrical conductor over at least a portion of the insulative layer. Block 830 may comprise disposing an illumination source at a distal portion of the malleable strip and in electrical communication with the flexible electrical conductor.

While there has been illustrated and/or described what are presently considered to be example features, it will be understood by those skilled in the relevant art that various other modifications may be made and/or equivalents may be substituted, without departing from claimed subject matter. Additionally, many modifications may be made to adapt a particular situation to the teachings of claimed subject matter without departing from the central concept(s) described herein. Therefore, it is intended that claimed subject matter not be limited to the particular examples disclosed, but that such claimed subject matter may also include all aspects falling within appended claims and/or equivalents thereof.

The terms, "and", "or", and "and/or" as used herein may include a variety of meanings that also are expected to depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein may be used to describe any feature, structure, and/or characteristic in the singular and/or may be used to describe a plurality or some other combination of features, structures and/or characteristics. Though, it should be noted that this is merely an illustrative example and claimed subject matter is not limited to this example.

What is claimed is:

1. A method of forming a surgical retractor, comprising:

forming a metallic strip, the metallic strip capable of being shaped among a first unbent configuration, a second bent configuration, and a configuration opposite the second bent configuration, the second bent configuration having a bend radius of approximately 0.75 cm to approximately 2.0 cm;

disposing an insulative layer over the metallic strip, wherein the insulative layer comprises a thickness of between approximately 0.1 mm and approximately 0.3 mm;

depositing an elastic and electrically conductive material over the insulative layer;

disposing, at a first end portion of the metallic strip, an illumination source in electrical communication with the elastic and electrically conductive material; and disposing an electronics module at a second end portion, opposite the first end portion, of the metallic strip, wherein the electronics module includes a press and hold switch to cause a plurality of incremental increases in intensity of the illumination source based on holding the switch in a depressed position.

2. The method of claim 1, wherein depositing the elastic and electrically conductive material comprises depositing the elastic and electrically conductive material along a middle portion of the metallic strip.

3. The method of claim 1, further comprising: disposing a light-adjusting layer to focus light from the illumination source toward a region normal to the illumination source.

4. The method of claim 1, wherein the elastic and electrically conductive material comprises a meandering conductive line, a spiral-shaped conductor, a conductive ink, or any combination thereof.

5. The method of claim 4, further comprising: coupling one or more conductive pads to the meandering conductive line, the spiral-shaped conductor, the conductive ink, or any combination thereof.

6. The method of claim 1, wherein the metallic strip comprises a width of between approximately 2.0 cm and approximately 5.0 cm and thickness of between approximately 0.5 mm and approximately 2.0 mm.

7. The method of claim 1, wherein the insulative layer substantially comprises thermoplastic polyurethane.

8. A method of forming a surgical retractor, comprising:

forming a strip from a malleable metallic material, the strip capable of being shaped among a first unbent configuration, a second bent configuration, and a configuration opposite the second bent configuration, the second bent configuration having a bend radius of approximately 0.75 cm to approximately 2.0 cm;

disposing an insulative layer over the strip;

depositing an elastic and electrically conductive material over the insulative layer; and disposing an additional layer of insulating material to permit the surgical retractor to be resistant to liquids encountered during surgical procedures, wherein the elastic and electrically conductive material conducts an electric current from a press and hold switch to an illumination source, and wherein the press and hold switch is to cause a plurality of incremental increases in illumination intensity based on holding the switch in a depressed position.

9. The method of claim 8, wherein the illumination source is a planar illumination source.

10. The method of claim 9, further comprising: disposing a light-adjusting layer that operates as a scattering medium over the planar illumination source.

11. The method of claim 10, wherein the light-adjusting layer operates to scatter a fraction of between approximately 3.0% and approximately 8.0% of the light generated by the planar illumination source.

12. The method of claim 11, wherein the light-adjusting layer comprises phosphorus particles, organic fluorescent dye, titanium dioxide particles, or combination thereof.

13. A method, comprising:

forming a strip from a malleable metallic material, the strip capable of being shaped among a first unbent configuration, a second bent configuration, and a configuration opposite the second bent configuration, the second bent configuration having a bend radius of approximately 0.75 cm to approximately 2.0 cm;

disposing an insulative layer over the strip;

depositing an elastic and electrically conductive material over the insulative layer;

disposing a press and hold switch at a first end portion of the strip to control an illumination source disposed at a second end portion of the strip, wherein the press and hold switch is to cause a plurality of incremental increases in illumination intensity based on holding the switch in a depressed position; and disposing a flexible charge storage module at the first end portion of the strip.

* * * * *